United States Patent [19]
Simpson et al.

[11] Patent Number: 5,951,541
[45] Date of Patent: *Sep. 14, 1999

[54] CHANNEL FORMING DEVICE WITH A SECURED DISTAL EXTREMITY

[75] Inventors: Carl J. Simpson, Los Altos; Randy J. Kesten, Mountain View; Manuel A. Javier, Santa Clara; Steve Pearce, Fremont; Sam G. Payne, Santa Clara; Kevin Gertner, San Jose, all of Calif.

[73] Assignee: Cardiogenesis Corporation, Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/486,978

[22] Filed: Jun. 7, 1995

[51] Int. Cl.$^6$ .................................................. A61B 17/36
[52] U.S. Cl. .................................................. 606/7; 606/15
[58] Field of Search .................................. 606/2, 13–17, 606/7, 10; 607/126, 108

[56] References Cited

U.S. PATENT DOCUMENTS

| | | | |
|---|---|---|---|
| 4,249,533 | 2/1981 | Komiya | 606/15 |
| 4,658,817 | 4/1987 | Hardy | 128/303.1 |
| 4,860,743 | 8/1989 | Abela | 606/16 X |
| 4,862,887 | 9/1989 | Weber et al. | 606/15 |
| 4,890,898 | 1/1990 | Bentley et al. | 606/16 X |
| 4,917,084 | 4/1990 | Sinofsky | 606/7 |
| 4,967,745 | 11/1990 | Hayes et al. | 606/15 X |
| 4,985,029 | 1/1991 | Hoshino | 606/16 |
| 5,037,421 | 8/1991 | Boutacoff et al. | 606/15 |
| 5,093,877 | 3/1992 | Aita et al. | 606/5 X |
| 5,125,926 | 6/1992 | Rudko et al. | 606/19 |
| 5,217,460 | 6/1993 | Knoepfler | 606/52 |
| 5,380,316 | 1/1995 | Aita et al. | 606/15 X |
| 5,389,096 | 2/1995 | Aita et al. | 606/7 X |
| 5,441,498 | 8/1995 | Perkins | 606/51 |
| 5,607,421 | 3/1997 | Jeevanandam et al. | 606/15 |
| B1 5,147,354 | 10/1997 | Boutacoff et al. | 606/15 |

OTHER PUBLICATIONS

Mirhoseini, et al., Clinical Report: "Laser Myocardial Revascularization," Lasers in Surgery and Medicine 6:459–461 (1986).
Mirhoseini, et al., "Lasers in Cardiothoracic Surgery," in Lasers in General Surgery (Joffe, Editor), Williams and Wilkins, 216–232 (1989).
Mirhoseini, et al., "New Concepts in Revascularization of the Myocardium," A Thorac. Surg. 45:415–420 (Apr. 1988).
Walter, et al., Europ. Surg. Res. 3: 130–138 (1971).
Mirhoseini, et al., "Myocardial Revascularization by Laser: A Clinical Report," Lasers in Surgery and Medicine 3:241–245 (1983).
Mirhoseini, et al., "Revascularization of the Heart by Laser," Journal of Microsurgery 253–260 (Jun. 1981).
Mirhoseini, "Laser Applications in Thoracic and Cardiovascular Surgery," Medical Instrumentation, vol. 17, No. 6, 401–403 (Nov.–Dec. 1982).
Mirhoseini, "Laser Revascularization of the Heart," in New Frontiers in Laser Medicine and Surgery (Atsumi, Editor), ISBN Elsevier Science Publishing Co., 296–303 (1982).
Mirhoseini, et al., "Transvenicular Revascularization by Laser," Lasers in Surgery and Medicine 2:187–198 (1982).

*Primary Examiner*—Robert L. Nasser
*Attorney, Agent, or Firm*—Heller Ehrman White & McAuliffe

[57] ABSTRACT

An intravascular device for forming a channel within a patient's ventricular wall which engages the tissue of the ventricular wall to prevent undesirable movement of the channel forming device while forming the channel.

8 Claims, 5 Drawing Sheets

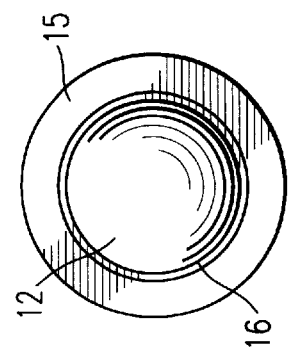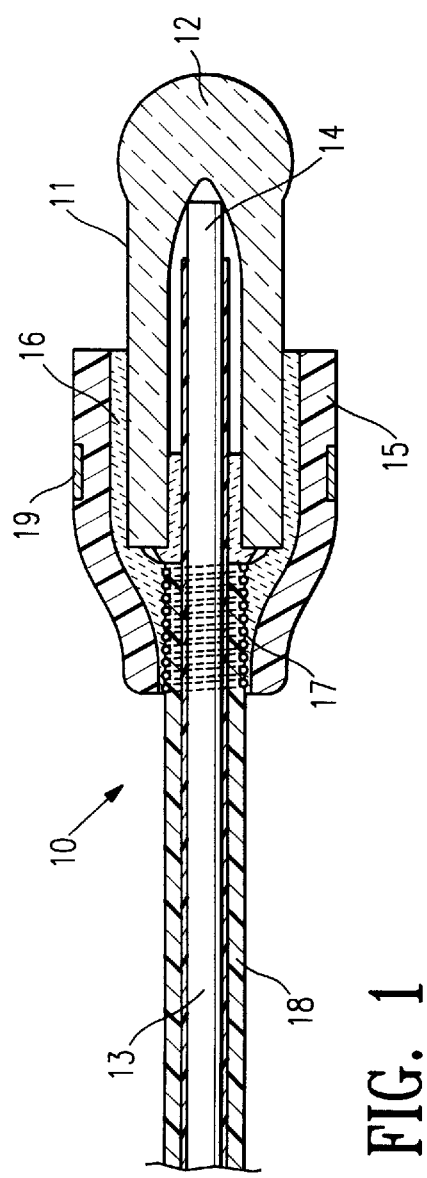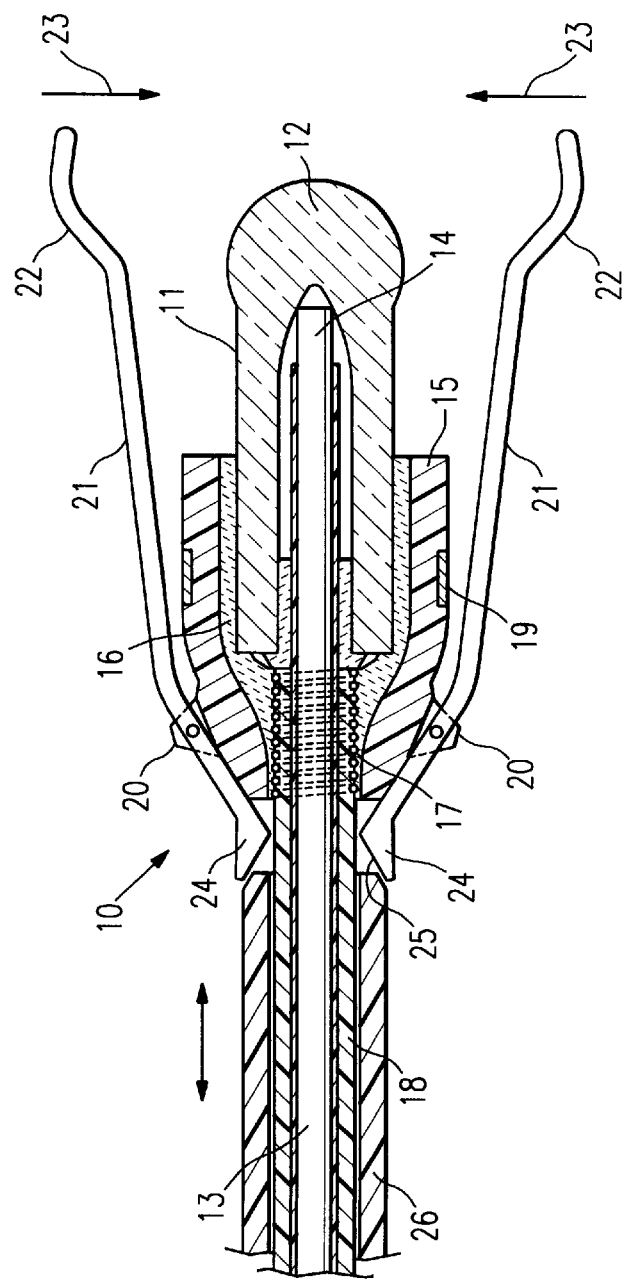

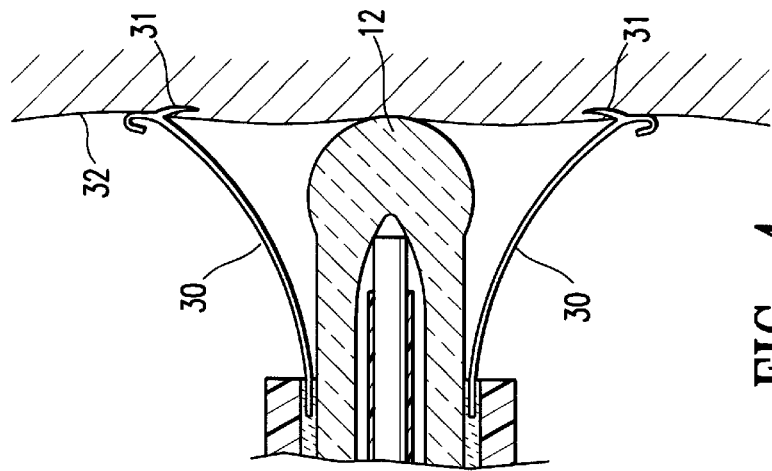
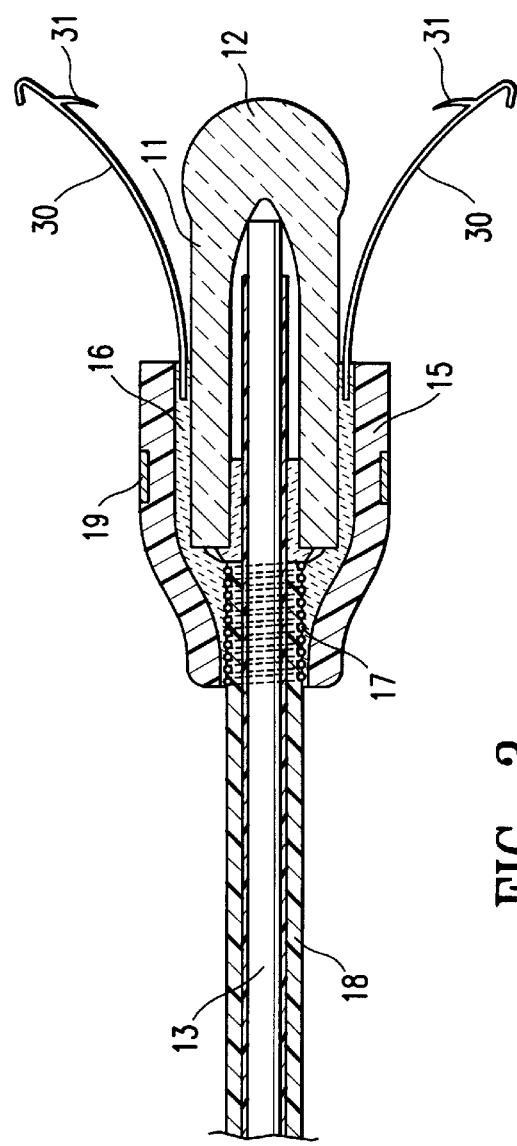

CHANNEL FORMING DEVICE WITH A SECURED DISTAL EXTREMITY

BACKGROUND OF THE INVENTION

This invention is directed to the formation of one or more channels into the wall of a patient's heart and particularly to a system for securing the optical fiber system while forming the channel in the patient's heart wall.

The channels formed in the wall of the patient's heart may be used in the treatment of heart tissue experiencing ischemic conditions by allowing increased perfusion of blood through the channel into the myocardium of a patient's heart. The formation of channels into the myocardium for improved perfusion into a patient's ischemic myocardial tissue is called myocardial revascularization. The first clinical trials of the revascularization process was made by Mirhoseini et al. See for example the discussions in Lasers in General Surgery (Williams & Wilkins; 1989), pp 216–223. Other early disclosures of this procedure is found in an article by Okada et al. in Kobe J. Med. Sci 32, 151–161, October 1986 and U.S. Pat. No. 4,658,817 (Hardy). These early references describe intraoperative revascularization procedures which require an opening in the chest wall and include formation of the channels through the epicardium.

Copending application Ser. No. 08/368,409, filed on Dec. 30, 1994 (Aita et al.), which is incorporated herein in its entirety, describes a percutaneous system for myocardial revascularization which is introduced through the patient's peripheral artery. The channels are formed through the endocardium into the myocardium. The channels formed in the ventricular wall may also be used for delivery of therapeutic or diagnostic agents, including agents for gene therapy.

While the percutaneous system for performing revascularization, developed by Aita et al., was a substantial advance, one of the difficulties found in forming the channel from within the patient's heart chamber was maintaining the distal end of the optical fiber against the endocardial wall. Apparently, acoustic energy created by the absorption of the laser energy emitted from the distal tip of the optical fiber system by the surrounding fluid, i.e. blood, can cause the distal end of the optical fiber system to be laterally displace away from the region of the endocardial surface in which the channel is to be formed. The distal tip of optical fiber tends to "skip" along the surface of the endocardial wall, thereby disabling channel formation. In European application Publication No. 0 515-867 A2 (Jeevanandam et al.) reference is made to providing suction means on a catheter into which the optical fiber system is slidably disposed to hold the position of the assembly adjacent to the ventricular wall. While this provides some benefit, it does not ensure that the distal tip of the optical fiber will remain in place when laser energy is transmitted to the tissue of the ventricular wall.

SUMMARY OF THE INVENTION

The present invention is directed to an improved laser based device for forming a channel in the wall of a patient's heart and particularly to a system which maintains the position of the distal end of the laser based system against the tissue of the heart wall to effectively transmit laser energy from an optical fiber or wave guide system to the heart tissue to form the channel.

The elongated laser energy transmitting system of the invention includes an elongated optical wave guide, such as an optical fiber, having a proximal end and a distal end and means to engage the tissue of the patient's endocardium so that there is no lateral displacement of the distal end of the optical wave guide from the location on the ventricular wall in which the channel is to be formed. One presently preferred means to engage the tissue of the patient's endocardium is to form the endocardial lining of the ventricular wall about at least a portion of the distal end of the wave guide. Another presently preferred means to engage the tissue is to provide one or more protuberances or cleats on the distal end of the optical wave guide press into the endocardial tissue when the optical wave guide is pressed against the ventricular wall. Both means effectively prevent lateral displacement or skipping of the distal end of the optical wave guide.

The laser energy transmitting system of the invention is percutaneously advanced through the patient's vasculature until the distal portion of the device is disposed within the left ventricle of the patient's heart. The distal tip of the optical wave guide is advanced toward the region of the ventricular wall where the channels are to be formed. With the distal tip of the optical fiber engaging the endocardial surface and the means to prevent the lateral excursion of the distal tip of the optical wave guide in place, the chances for a lateral excursion or movement of the distal tip of the optical wave guide is effectively prevented.

These and other advantages of the invention will become more apparent from the following detailed description of the invention, when taken in conjunction with the accompanying exemplary drawings.

BRIEF DESCRIPTION OF THE DRAWINGS

FIG. 1 is a longitudinal cross-sectional view of the distal portion of an optical fiber apparatus.

FIG. 1A is an end view of the optical fiber system shown in FIG. 1.

FIG. 2 is a longitudinal cross-sectional view of the distal portion of an optical fiber similar to that shown in FIG. 1 except that a mechanism is shown for grasping surface endocardial tissue of a patient's heart.

FIG. 3 is a longitudinal cross-sectional view of another embodiment similar to that show in FIG. 2 with different means to grasp the endocardial surface of a ventricular wall of the patient's heart.

FIG. 4 is a partial view of the device shown in FIG. 3 with the barbs or cleats engaging the endocardial tissue.

DETAILED DESCRIPTION OF THE INVENTION

Figure 5A:
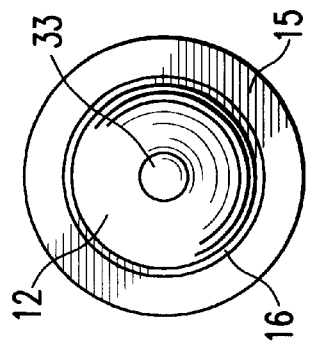
FIG. 5A is an end view of the embodiment shown in FIG. 5.

FIGS. 1 and 1A illustrates an optical fiber system 10, suitable for use in the present invention, having an elongated probe tip 11 with a lens 12 on its distal, an elongated optical fiber shaft 13 with a distal end 14 disposed and secured within the interior of the probe tip and an outer support member or lens capsule 15 secured to the optical fiber shaft by means of adhesive 16. A helical metallic coil 17 is provided on the exterior of the optical fiber shaft 13 at a location proximal to the probe tip to facilitate securing the outer support member to the shaft. The outer surface of the shaft 13 is provided with a lubricous surface or jacket 18 such as a fluoropolymer (Tefzel). The metallic coil 17, which may be made of suitable material such a NiTi alloy or stainless steel, is tightly wound against the lubricous surface 18 to provide a good bond and then the outer support member may be shrunk fit or otherwise bonded to the coil by a suitable adhesive 16. A radiopaque cylindrical marker 189 is provided on the outer support member 15 to facilitate fluoroscopic observation within the patient.

In the embodiment shown in FIG. 2 the outer tubular support member 15 is provided with a plurality of brackets 20 to which fingers, jaws or other grabbing means 21 are rotatable mounted. The distal extremities 22 of the fingers 21 are shaped to readily grasp endocardial tissue when the distal extremities of the fingers are urged together as shown by the arrows 23. While only two fingers 21 are shown three or more fingers may be employed. The proximal extremities 24 of the fingers 21 are provided with an inclined surface 25 so that distal movement of sheath 26 presses the sheath against the inclined surfaces and thereby causes the distal extremities to be urged together to grasp the surface of the endocardium so that the lens 12 engages the grasped endocardial tissue and any undesirable movement of the optical fiber 10 is prevented.

In FIG. 3, spring loaded members 30 are secured to the probe tip 11 and extend distally to the lens 12 and have distal extremities with barbs 31 or other projections which engage the endocardial lining 32, as shown in FIG. 4, to hold the lens 12 against the endocardial lining while laser energy is transmitted thereto.

Figure 5:
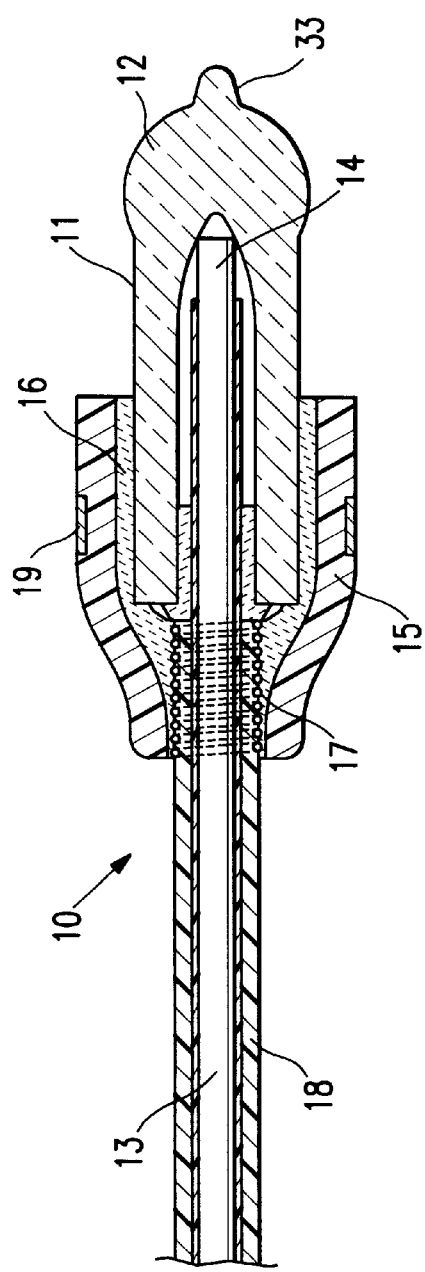
FIG. 5. is a longitudinal cross-sectional view of an alternative embodiment of the invention wherein a protuberance or cleat is provided in the distal tip of the optical fiber system which presses into the endocardial tissue.
Figure 6:
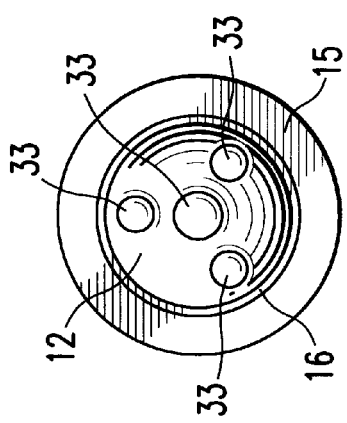
FIG. 6 is an end view of an alternative embodiment similar to that shown in FIGS. 5A and 6B except that multiple protuberances are provided on the distal tip of the optical fiber system.

The embodiment shown in FIGS. 5 and 5A has a lens with a protuberance or cleat 33 extending out therefrom, so that when the lens is pressed against the endocardial lining the protuberance 33 is pressed deeply into the tissue to prevent undesirable movement. The protuberance 33 has little or no detrimental effects on the transmission of laser energy because there is a slight divergence of the laser beam as it is emitted from the lens. Multiple protuberances 33 may be used as shown in FIG. 6.

Figure 7A:
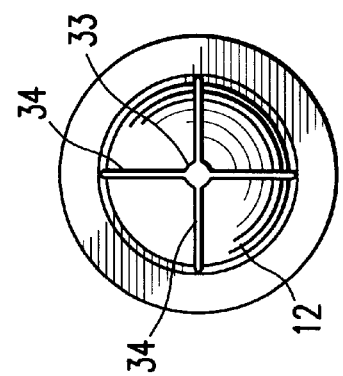
FIG. 7A is an end view of the embodiment shown in FIG. 7.
Figure 7:
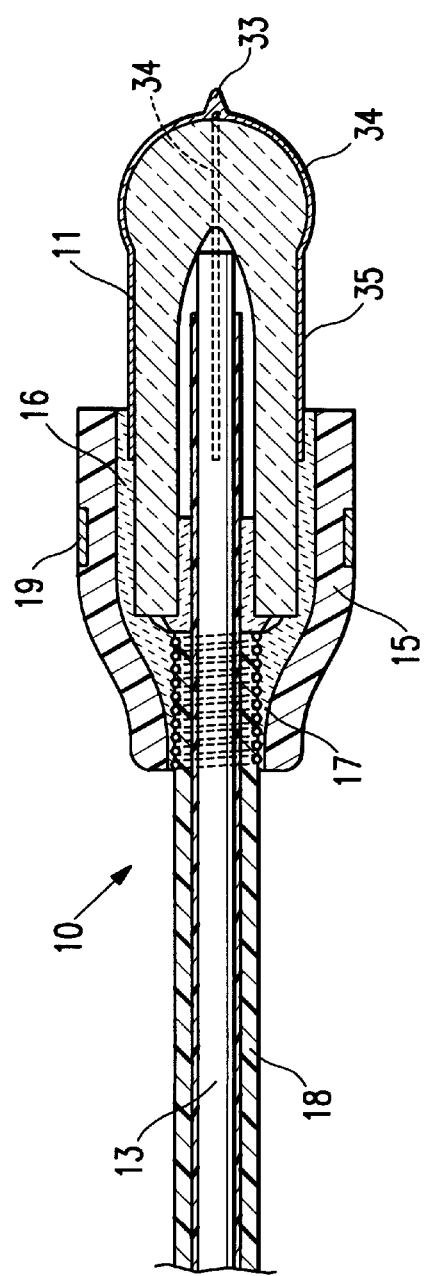
FIG. 7 is a longitudinal cross-sectional view of another alternative embodiment wherein a protuberance and ridges are provided on the distal tip of the optical wave guide.

The lens 12 may be also provided with one or more ridges 34 in lieu or in addition to the protuberance 33 such as shown in FIGS. 7 and 7A. In the embodiment shown in these figures the ridges 34 and the cleat 33 are formed of a gold plated, stainless steel open framework or cot 35 which fits over the probe tip 11 as shown. The proximal end of the open framework 35 fits into the distal end of the outer support member and is secured by the adhesive 16.

Figure 8A:
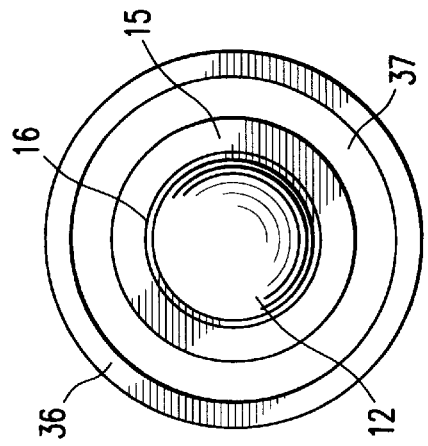
FIG. 8 is a longitudinal cross-sectional view of another alternative embodiment of the invention wherein an outer sheath is provided which is connected to a vacuum source so that when the sheath is pressed against the endocardial surface and a vacuum is established within the inner lumen of the sheath, endocardial tissue is pulled into the space.
Figure 8:
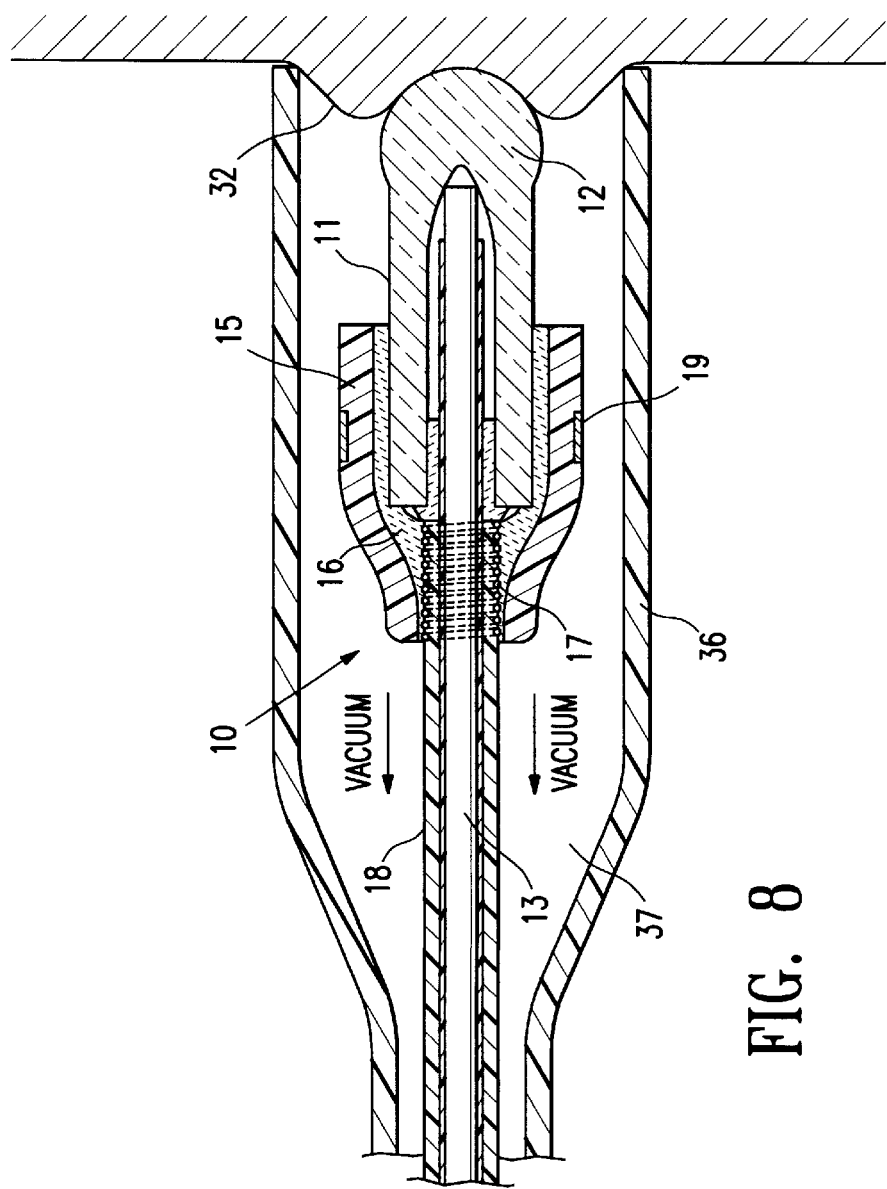

Another alternative embodiment is shown in FIGS. 8 and 8A where an outer sheath 36 is provided about the optical fiber system 10 having an interior 36 in fluid communication with a vacuum source (not shown). When the sheath 35 is pressed against the endocardium 32 and a vacuum is generated within the interior 36, tissue from the endocardium is aspirated or sucked into the interior 36 of the sheath 35, engaging the lens 12 as shown and ensuring little or no undesirable movement by the optical fiber system when delivering laser energy to the endocardium to form a channel.

Details of forming the channel within the ventricular wall and optical fiber devices therefor are disclosed in copending application Ser. No. 08/368,409, filed Dec. 20, 1994, Ser. No. 08/379,002, filed Jan. 27, 1995, and Ser. No. (unassigned), filed on Jun. 7, 1995, entitled OPTICAL FIBER FOR MYOCARDIAL CHANNEL FORMATION (S. G. Payne et al.) which are incorporated herein in their entireties.

Unless noted otherwise, the various components of the embodiments of the invention may be made of conventional materials used in intravascular catheters and other devices. For example, the outer support member 15 may be formed of polyethylene terephthalate, the adhesive 15 may be a UV cured adhesive such as Dymak 198-m, the optical fiber may be formed of fused silica (low—OH) and the probe tip may be formed of fused quartz. As will be apparent to those skilled in the art a variety of materials both conventional and novel may be used in the present invention.

Although individual features of embodiments of the invention may be shown in some of the drawings and not in others, those skilled in the art will recognize that individual features of one embodiment of the invention can be combined with any or all the features of another embodiment. Moreover, while the invention is described herein in terms of using a laser based device for forming a channel within a patient's ventricular wall, the advantages of the present invention can be obtained to a greater or lesser degree in a variety of channel forming devices such as rotating abrading devices, heated probes, high frequency (e.g. RF or microwave) heating devices, induction heating devices, high pressure water streams, and the like. Other modifications and improvements can be made to the invention without departing from the scope thereof.

What is claimed is:

1. A system for forming a channel within a ventricular wall of a patient's heart from within a chamber defined by an interior surface of the ventricular wall, comprising:

a) an elongated, laser energy transmitting system having a distal end for emitting laser energy and being configured for percutaneous delivery by introduction into a peripheral artery and advancement to the interior of the ventrical through the patient's vasculature; and b) at least two distally extending elongated members which are configured to engage the interior surface of the ventricular wall to urge tissue of the ventricular wall between the elongated members toward the distal end of the laser energy transmitting system upon the inward motion thereof to ensure contact between the distal end of the laser energy transmitting system and the interior surface of the ventricular wall when laser energy is emitted from the distal end of the laser energy transmitting system and which are configured so that the elongated members do not pass in front of the distal end of the laser energy transmitting system which emits laser energy; and c) an actuator operatively coupled to the distally extending elongated members for causing inward motion thereof.

2. The system of claim 1 wherein the elongated members are pivotally mounted on the distal extremity of the laser energy transmitting system.

3. The system of claim 2 wherein an outer sheath slidable over the laser energy transmitting system engages the proximal extremities of the pivotally mounted elongated members and urges the distal extremities of the elongated members toward each other to thereby grasp the interior surface of the ventricular wall.

4. The system of claim 1, wherein the elongated members are provided with inwardly projecting barbs for engaging and thereby grasping the interior surface of the vascular wall.

5. The system of claim 1 wherein a sheath having a distal end configured to engage the interior surface of the ventricular wall, being disposed about the elongated, laser energy transmitting system and having an interior chamber which is in fluid communication with a vacuum source so that when the distal end of the sheath engages the interior surface of the ventricular wall and a vacuum is applied to the interior of the sheath that tissue of the endocardium is pulled into the interior of the sheath thereby preventing undesirable movement of the distal end of the laser energy transmitting system.

6. The system of claim 1 wherein the distal end of the laser transmitting system is provided with at least one distally extending protuberance to engage the interior surface of the ventricular wall.

7. The system of claim 1 wherein the distal end of the laser transmitting system is provided with at least one projecting ridge to engage the interior surface of the ventricular wall.

8. A system for forming a channel within a ventricular wall of a patient's heart from within a chamber defined by an interior surface of the ventricular wall, comprising:

a) an elongated, channel forming system having means on a distal end thereof for forming a channel and being configured for percutaneous delivery by introduction into a peripheral artery of the patient and advancement to the interior of the ventrical through the patient's vasculature; and b) at least two distally extending elongated members which have distal end configured to engage the interior surface of the ventricular wall and to urge tissue of the ventricular wall between the distal ends of the elongated members toward the distal end of the channel forming system upon the inward motion thereof to ensure contact between the distal end of the channel forming system and the interior surface of the ventricular wall when the channel is being formed and which are configured such that the inward motion thereof is mechanically limited so that the elongated members are prevented from passing in front of a channel path of the channel forming means; and c) an actuator operatively coupled to the distally extending elongated members for causing inward motion thereof.

\* \* \* \* \*